United States Patent [19]

Voyta et al.

[11] Patent Number: 5,145,772
[45] Date of Patent: Sep. 8, 1992

[54] CHEMILUMINESCENCE ENHANCEMENT OF ENZYME-ACTIVATED DECOMPOSITION OF ENZYMATICALLY CLEAVABLE CHEMILUMINESCENT 1,2-DIOXETANES

[75] Inventors: John C. Voyta, North Reading; Brooks Edwards, Cambridge; Irena Y. Bronstein, Newton; Patricia McGrath, Cambridge, all of Mass.

[73] Assignee: Tropix, Inc., Bedford, Mass.

[21] Appl. No.: 767,566

[22] Filed: Sep. 30, 1991

Related U.S. Application Data

[63] Continuation of Ser. No. 203,263, Jun. 1, 1988, Pat. No.

[51] Int. Cl.$^5$ .............................................. C12Q 1/00
[52] U.S. Cl. .................................... 435/4; 252/700; 424/7.1; 435/5; 435/6; 435/7.1; 435/7.4; 435/7.91; 435/11; 435/14; 435/7.9; 435/960; 436/71; 436/95; 436/172; 436/537; 436/800; 436/805; 436/827
[58] Field of Search .............. 436/71, 95, 172, 536, 436/537, 800, 805, 827; 435/4-6, 7.1, 7.4, 7.9, 7.91, 11, 14, 960; 250/459.1, 461.2; 252/700; 424/2, 3, 7.1

[56] References Cited

U.S. PATENT DOCUMENTS

| 4,645,646 | 2/1987 | Gadow et al. ............... 436/808 X |
| 4,729,950 | 3/1988 | Kricka et al. |
| 4,857,652 | 8/1989 | Schaap ..................... 549/511 X |
| 4,927,769 | 5/1990 | Chang et al. ................ 436/805 X |

(List continued on next page.)

FOREIGN PATENT DOCUMENTS

| 175889 | 2/1985 | European Pat. Off. |
| 0210449 | 4/1987 | European Pat. Off. |
| 0219352 | 4/1987 | European Pat. Off. |
| 0046563 | 3/9182 | European Pat. Off. |
| 2063469 | 6/1981 | United Kingdom . |
| 2165354 | 4/1986 | United Kingdom . |
| 2196118 | 4/1988 | United Kingdom . |
| 2205945 | 12/1988 | United Kingdom . |

OTHER PUBLICATIONS

Zaklika, K. A., et al. J. Amer. Chem. Soc., 100, 328 (1978).
McCapra, F., et al. J. Chem. Soc., Chem. Commun., 944 (1977).

(List continued on next page.)

*Primary Examiner*—Robert J. Hill, Jr.
*Attorney, Agent, or Firm*—Oblon, Spivak, McClelland, Maier & Neustadt

[57] ABSTRACT

Water soluble naturally-occurring and synthetic enhancer substances, generally macromolecular in nature, for example globular proteins that include hydrophobic regions such as bovine serum albumin, and polymeric quaternary ammonium salts such as poly(vinylbenzyltrimethylammonium chloride), which have the ability to inhibit light-emitting fluorophores resulting from the decomposition of chemiluminescent compounds from releasing energy through non-light emitting pathways, are disclosed as permitting the stabilization, and hence increasing the light intensity, of such light-emitting fluorophores in aqueous media as compared to the intensity of the light emitted by the same quantities of such fluorophores in aqueous media in the absence of such enhancer substances. Any chemiluminescent enzymatically cleavable 1,2-dioxetane, for example 3-(2'-spiroadamantane)-4-methoxy-(3"-phosphoryloxy)phenyl-1,2-dioxetane disodium salt, can be used. Auxiliary fluorophores, for example fluorescein and derivatized fluoresceins, that accept energy from fluorophores produced by decomposition of a chemiluminescent compound and in turn emit detectable energy, can also be present. Such enhancer substance/chemiluminescent compound compositions are useful in detecting the presence or determining the concentration of chemical or biological substances in immunoassays, chemical assays and nucleic acid probe assays, and in chemical/physical probe procedures for studying the microstructures of macromolecules.

36 Claims, 6 Drawing Sheets

U.S. PATENT DOCUMENTS

| | | | |
|---|---|---|---|
| 4,931,223 | 6/1990 | Bronstein et al. | 435/6 X |
| 4,952,707 | 8/1990 | Edwards et al. | 436/172 X |
| 4,959,182 | 9/1990 | Schaap | 435/6 X |
| 4,978,614 | 12/1990 | Bronstein | 435/125 X |

OTHER PUBLICATIONS

Hummelen, J. C., et al. Methods in Enzymology, vol. 133, 531–57 (1968).

Matthews, J. A. et al. Anal. Biochem. 151:205–9 (1985).

Hummelen, J. C., et al. Pure & Appl. Chem., vol. 5, No. 5, pp. 639–650 (1987).

Messeri, G., et al., Clin. Chem., 30:653 (1984).

Kubota, et al; Bull. Chem. Soc. Japan, 46, pp. 100–103; (1973).

Schore, et al; J. Am. Chem. Soc.; 96:1; pp. 306—308; (1974).

Phol; Z. Naturforsch; 31c; pp. 575–588; (1976).

Kricka, et al; Arch. Biochem. Biophys.; 217-2; pp. 674–681; (1982).

CHEMILUMINESCENCE ENHANCEMENT OF ENZYME-ACTIVATED DECOMPOSITION OF ENZYMATICALLY CLEAVABLE CHEMILUMINESCENT 1,2-DIOXETANES

This application is a continuation of application Ser. No. 07/203,263, filed Jun. 1, 1988, now abandoned, which in turn is a continuation-in-part of application Ser. No. 06/889,823, filed Jun. 24, 1986, pending.

FIELD OF THE INVENTION

This invention relates to improvements in the detectability of electromagnetic, including optically detectable, energy released by the decomposition of chemiluminescent chemical compounds in aqueous media. More particularly, this invention relates to enhanced detection of electromagnetic energy released by the decomposition of chemiluminescent compounds used to determine the presence, concentration or structure of a substance in an aqueous sample, particularly when such chemiluminescent compounds are used to detect the presence or determine the concentration of chemical or biological substances by art-recognized immunoassay techniques, chemical assays or nucleic acid probe assays, or when they are used as direct chemical/physical probes for studying the molecular structures or microstructures of various macromolecules: synthetic polymers, proteins, nucleic acids and the like.

BACKGROUND OF THE INVENTION

The decomposition of chemiluminescent chemical compounds to release electromagnetic, and especially optically detectable, energy—usually luminescence in the form of visible light—is well known and understood. The incorporation of such light emitting reactants in art-recognized immunoassays, chemical assays, nucleic acid probe assays and chemical/physical probe techniques as the means by which the analyte, a substance whose presence, amount or structure is being determined, is actually identified or quantified has assumed increasing importance in recent years, particularly with the advent of enzymatically-cleavable 1,2-dioxetanes; see, for example, copending Bronstein U.S. patent application Ser. No. 889,823, "Method of Detecting a Substance Using Enzymatically-Induced Decomposition of Dioxetanes", filed Jul. 24, 1986; Bronstein et al U.S. patent application Ser. No. 140,035, "Dioxetanes for Use in Assays", filed Dec. 31, 1987 and Edwards U.S. patent application Ser. No. 140,197 "Synthesis of 1,2-Dioxetanes and Intermediates Therefor", filed Dec. 31, 1987.

Reactions that produce chemiluminescence exemplify yet another instance in which the medium, although not the message, can determine the intensity of the message transmitted. Chemiluminescent compounds that, upon decomposition in substances such as moderately polar or polar aprotic organic solvents, e.g., n-butanol, acetonitrile, dimethylsulfoxide or dimethylformamide, produce fluorophores that in turn emit light of adequate intensity for easy detection and quantitation will produce light of considerably lessened intensity when decomposed in a polar protic environment, and especially in aqueous media. But since all biological systems are aqueous—indeed, man himself is 97% water—the need to enhance the intensity of light produced by chemiluminescent labels or substrates in immunoassays, nucleic acid probe assays, chemical/physical probe techniques and other bioassays is obvious. One way to provide such enhancement, of course, is to use expensive optical or electronic equipment: single photon counters, luminometers, scintillation counters, etc. The present invention provides a far less expensive yet equally effective way of providing the needed light enhancement in aqueous media, and in many cases provides enhanced light intensity to a degree which permits detection by simple, inexpensive means, such as with a camera, instead of with complex detection instruments.

The present invention also permits the detection of lesser concentrations of analytes using the same quantities of chemiluminescent chemical compounds used in hitherto-practiced methods, and concomitantly permits the use of lessened amounts of chemiluminescent chemical compounds to detect the same concentrations of analytes as compared to those necessary in hitherto-practiced methods. B practicing this invention the intensity of light emitted by fluorophore decomposition products of chemiluminescent chemical compounds can be enhanced by a factor of at least !0%, but usually at least tenfold and oftentimes by factors of at least 100 to 1,000,000 times the intensities obtainable in aqueous media using the same chemiluminescent compounds in hitherto-practiced methods.

While we do not wish to be bound by any theory or mechanism advanced to explain the operation of this invention, we believe that our enhancer substances act in a polar protic environment, such as an aqueous medium, to bind fluorophore-containing fragments resulting from the decomposition of a chemiluminescent chemical compound and maintain such fragments in a stabilized conformation, possibly by hydrophobic or ionic interaction, or both, between the enhancer substance and the fluorophorecontaining fragment. This we believe in turn inhibits the fluorophore from releasing all or a substantial part of its excitational energy through non-light emitting pathways: vibrational relaxation in which energy is emitted as heat rather than light, intersystem crossing to other lower energy states, or other such mechanisms.

SUMMARY OF THE INVENTION

It has now been discovered that certain water soluble naturally-occurring and synthetic substances, generally macromolecular in nature, for example water soluble globular proteins that include hydrophobic regions: mammalian serum albumins such as bovine serum albumin (BSA) and human serum albumin (HSA), or water soluble polymeric quaternary ammonium salts: poly(vinylbenzyltrimethyl-ammonium chloride) (TMQ) or poly[vinylbenzyl(benzyldimethyl-ammonium chloride)] (BDMQ), permit the stabilization, and hence increase the light intensity, of light-emitting fluorophores produced by the decomposition of chemiluminescent chemical compounds in aqueous media. Such chemiluminescent compounds are enzymatically cleavable 1,2-dioxetanes; and mixtures of such chemiluminescent compounds with each other and with one or more auxiliary fluorophores, e.g., fluorescein, that accept energy from energy-emitting fluorophores produced by the decomposition of chemiluminescent compounds and in turn emit detectable energy. By virtue of the presence of effective amounts of an enhancer substance or substances the intensity of the light emitted in aqueous medium by the thus-stabilized fluorophores is increased significantly as compared to the intensity of light emitted by the same quantities of fluorophores in the absence of such enhancers.

It is, therefore, an object of this invention to provide improvements in the detectability of electromagnetic, e.g., optically detectable, energy released by the decomposition of chemiluminescent chemical compounds in aqueous media.

Another object of this invention is to provide means for enhanced detection of electromagnetic, e.g., optically detectable, energy released by the decomposition of chemiluminescent chemical compounds used to detect the presence or determine the concentration or structure of a substance in an aqueous sample.

A further object of this invention is to provide improvements in the detectability of electromagnetic, e.g., optically detectable, energy released by the decomposition of chemiluminescent chemical compounds used to detect the presence or determine the concentration of chemical or biological substances by art-recognized immunoassay, chemical assay or nucleic acid probe assay techniques.

A still further object of this invention is to provide improvements in the detectability of electromagnetic, e.g., optically detectable, energy released by the decomposition of chemiluminescent chemical compounds for studying molecular structures or microstructures.

Yet another object of this invention is to provide aqueous compositions comprising water soluble naturally-occurring and synthetic enhancer substances which enable the stabilization, and hence increase the light intensity, of light-emitting fluorophores produced by the decomposition of chemiluminescent chemical compounds in aqueous media.

These and other objects, as well as the nature, scope and utilization of this invention, will become readily apparent to those skilled in the art from the following description, the drawings and the appended claims.

BRIEF DESCRIPTION OF THE DRAWINGS

FIG. 2) and Example 7 (1.0% BSA; FIG. 3), together with the luminescence rate spectrum of Example 30's buffer control (FIG. 4).

DETAILED DESCRIPTION OF THE INVENTION

Figure 1:
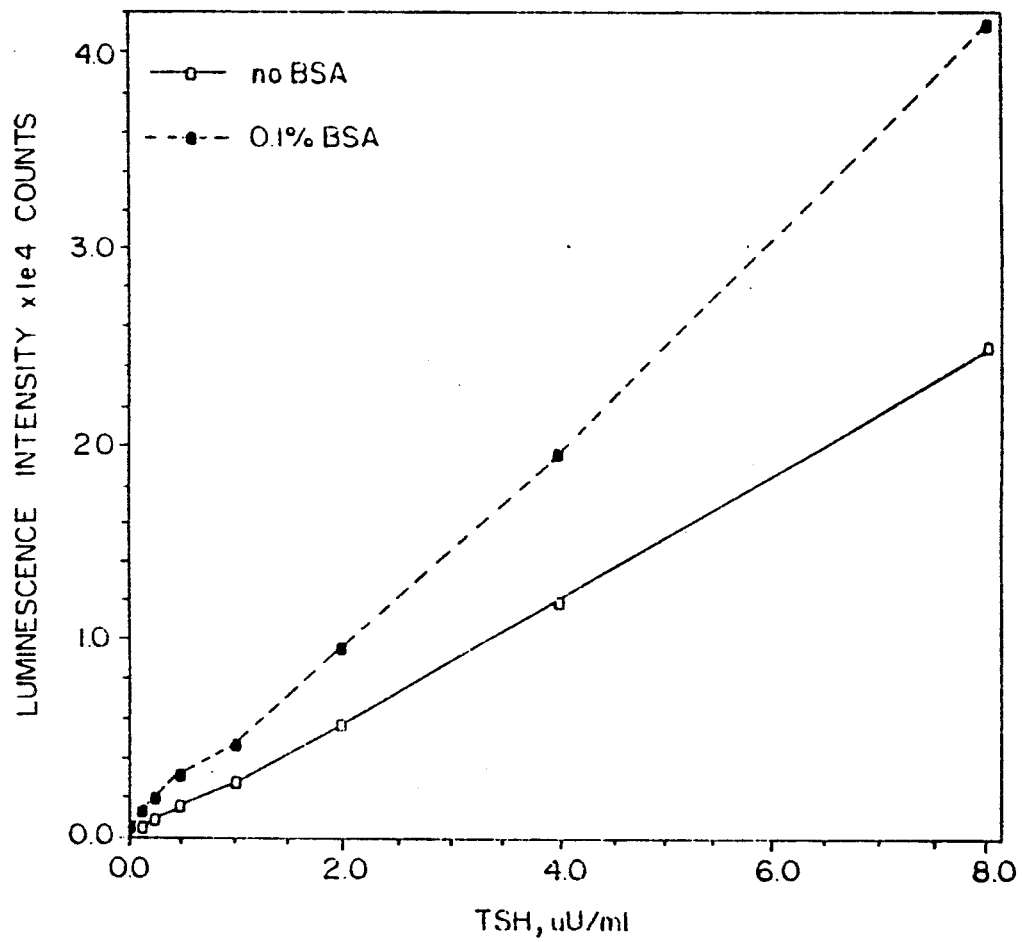
FIG. 1 shows plots of the luminescense intensity signals obtained in the TSH assays of Example 46 performed in the presence (Curve "A") and absence (Curve "B") of BSA.

The enhancer substances used in practicing this invention are water soluble naturally-occurring or synthetic materials which can provide a hydrophobic microenvironment of reduced polarity for fluorophore-containing fragments resulting from the decomposition of a chemiluminescent chemical compound contained in a polar medium, i.e., a medium consisting of water as a solvent or a mixture of water and other largely or entirely polar substances, such as methanol, acetonitrile, dimethylsulfoxide, dimethylformamide, or the like.

As noted above, included among such enhancer substances are macromolecular globular proteins, generally ones having molecular weights ranging from about 1000 to about 600,000 daltons, and preferably from about 40,000 to about 100,000 daltons, as determined by SDS gel electrophoresis, that include hydrophobic regions: mammalian serum albumins such as BSA, HSA and the like; globular proteins such as mammalian IgG, IgE, Protein A, avidins, and the like; serum lipoproteins, apolipoproteins, and the like.

Synthetic oligomeric or polymeric enhancer substances that can be used in practicing this invention include, first of all, water soluble poly(vinylaryl quaternary ammonium salts), such as the poly(vinylbenzyl quaternary ammonium salts) having the formula:

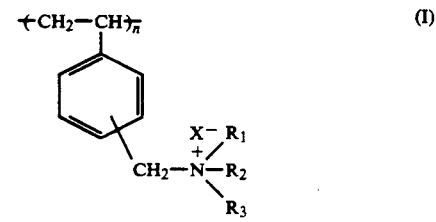

In this formula each of $R_1$, $R_2$ and $R_3$ can be a straight or branched chain unsubstituted alkyl group having from 1 to 20 carbon atoms, inclusive, e.g., methyl, ethyl, n-butyl, t-butyl, cetyl, or the like; a straight or branched chain alkyl group having from 1 to 20 carbon atoms, inclusive, substituted with one or more hydroxy, alkoxy, e.g., methoxy, ethoxy, benzyloxy or polyoxethylethoxy, aryloxy, e.g., phenoxy, amino or substituted amino, e.g., methylamino, amido, e.g., acetamido or cholesteryloxycarbonylamido, or fluoroalkane or fluoroaryl, e.g., heptafluorobutyl, groups, an unsubstituted monocycloalkyl group having from 3 to 12 ring carbon atoms, inclusive, e.g., cyclohexyl or cyclooctyl, a substituted monocycloalkyl group having from 3 to 12 ring carbon atoms, inclusive, substituted with one or more alkyl, alkoxy or fused benzo groups, e.g., methoxycyclohexyl or 1,2,3,4-tetrahydronaphthyl, a polycycloalkyl group having 2 or more fused rings, each having from 5 to 12 carbon atoms, inclusive, unsubstituted or substituted with one or more alkyl, alkoxy or aryl groups, e.g., 1-adamantyl or 3-phenyl-1-adamantyl, an aryl, alkaryl or aralkyl group having at least one ring and from 6 to 20 carbon atoms in toto, unsubstituted or substituted with one or more alkyl, aryl, or fluoroalkane or fluoroaryl groups, e.g., phenyl, naphthyl, pentafluorophenyl, ethylphenyl, benzyl, hydroxybenzyl, phenylbenzyl or dehydroabietyl; at least two of $R_1$, $R_2$ and $R_3$, together with the quaternary nitrogen atom to which they are bonded, can form a saturated or unsaturated, unsubstituted or substituted nitrogen-containing, nitrogen and oxygen-containing or nitrogen and sulfur-containing ring having from 3 to 5 carbon atoms, inclusive, and 1 to 3 heteroatoms, inclusive, and which may be benzoanylated, e.g., 1-pyridyl,1-(3-alkyl or aralkyl)imidazolium, morpholino, piperidino or acylpiperidino, benzoxazole, benzthiazole or benzamidazole.

The symbol $X^-$ represents a counterion which can include, alone or in combination, moieties such as halide, i.e., fluoride, chloride, bromide or iodide, sulfate, alkylsulfonate, e.g., methylsulfonate, arylsulfonate, e.g., p-toluenesulfonate, substituted arylsulfonate, e.g., anilinonaphthylenesulfonate (various isomers), lucifer yellow CH and diphenylanthracenesulfonate, perchlorate, alkanoate, e.g., acetate, arylcarboxylate, e.g., fluorescein or fluorescein derivatives, benzoheterocyclicarylcarboxylate, e.g., 7-diethylamino-4-cyanocoumarin-3-carboxylate, phosphate, or substituted monoaryloxyphosphate, e.g., a 3-(2'-spiroadamantane)-4-methoxy-(3''-phosphoryloxy)phenyl-1,2-dioxetane dianion or other dianions indicated in formula III, infra.

The symbol n represents a number such that the molecular weight of such poly(vinylbenzyl quaternary ammonium salts) will range from about 800 to about 200,000, and preferably from about 20,000 to about 70,000, as determined by intrinsic viscosity or LALLS techniques.

Illustrative of such water soluble poly(vinylbenzyl quaternary ammonium salts) are TMQ, BDMQ, and the like.

These vinylbenzyl quaternary ammonium salt polymers can be prepared by free radical polymerization of the appropriate precursor monomers or by exhaustive alkylation of the corresponding tertiary amines with polyvinylbenzyl chloride. This same approach can be taken using other polymeric alkylating agents such as chloromethylated polyphenylene oxide or polyepichlorohydrin. The same polymeric alkylating agents can be used as initiators of oxazoline ring-opening polymerization, which, after hydrolysis, yields polyethyleneimine graft copolymers. Such copolymers can then be quaternized, preferably with aralkyl groups, to give the final polymeric enhancer substance.

Water soluble acetals of a polyvinylalcohol and a formylbenzyl quaternary ammonium salt, having the formula:

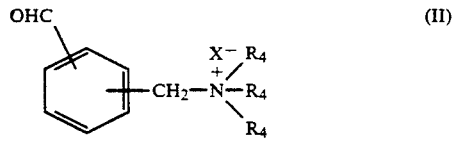

(II)

wherein each $R_4$ is the same or a different aliphatic substituent and $X_1$ is an anion, as disclosed and claimed in Bronstein-Bonte et al U.S. Pat. No. 4,124,388, can also be used as enhancer substances in practicing this invention. And, the individual vinylbenzyl quaternary ammonium salt monomers used to prepare the poly(vinylbenzyl quaternary ammonium salts) of formula I above can also be copolymerized with other vinylbenzyl quaternary ammonium salt monomers whose polymers are depicted in formula I, or with other ethylenically unsaturated monomers having no quaternary ammonium functionality, to give polymers such as those disclosed and claimed in Land et al U.S. Pat. No. 4,322,489; Bronstein-Bonte et al U.S. Pat. No. 4,340,522, Land et al U.S. Pat. No. 4,424,326; Bronstein-Bonte et al U.S. Pat. No. 4,503,138 and Bronstein-Bonte U.S. Pat. No. 4,563,411, all of which polymers can also be used as enhancer substances in practicing this invention. Preferably these quaternized polymers will have molecular weights within the ranges given above for the poly(vinylbenzyl quaternary ammonium salts) of formula I.

Other water soluble oligomeric, homopolymeric and copolymeric materials can be used as enhancer substances in addition to or instead of the foregoing polymers, including:

poly-N-vinyl oxazolidinones;

polyvinyl carbamates (e.g., polyvinyl propylene carbamate);

polyhydroxyacrylates and methacrylates [e.g., poly($\beta$-hydroxyethyl)methacrylate and polyethyleneglycol monomethacrylates];

amine-containing oligomers (e.g., Jeffamines) quaternized with alkylating or aralkylating agents;

synthetic polypeptides (e.g., polylysine co phenylalanine);

polyvinylalkylethers (e.g., polyvinyl methyl ether);

polyacids and salts thereof [e.q., polyaorylic acids, polymethacrylic acids, polyvinylbenzoic acid, polyethylenesulfonic acid, polyacrylamidomethylpropanesulfonic acid, polymaleic acid and poly(N-vinyl succinamidic acid)];

polyacrylamides and polymethacrylamides derived from ammonia or cyclic and acyclic primary or secondary amines;

polyvinyl alcohol and polyvinyl alcohol copolymers with vinyl acetate, ethylene and the like;

poly 2-, 3- or 4-vinylpyridinium salts where the heterocyclic nitrogen atom is bonded to a group as defined for $R_1$ $R_2$ and $R_3$ in formula I above;

polyvinylalkylpyrrolidinones (e.g., polyvinylmethylpyrrolidinones);

polyvinylalkyloxazolidones (e.g., polyvinylmethyloxazolidones);

branched polyethyleneimines, acylated branched polyethyleneimines, or acylated branched polyethyleneimines further quaternized with alkyl or aralkyl groups;

poly N-vinylamines derived from ammonia or cyclic and acyclic primary or secondary amines, and salts thereof;

polyvinylpiperidine;

polyacryloyl, polymethacryloyl or 4-vinylbenzoyl aminimides where the three substituents on the positively charged nitrogen atom may be any of the $R_1$, $R_2$ and $R_3$ groups defined in formula I above.

Here too, these oligomeric or polymeric enhancer substances preferably will have molecular weights within the ranges given above for the poly(vinylbenzyl quaternary ammonium salts) of formula I.

Water soluble monomeric quaternary soaps whose nitrogen atom has at least one benzyl substituent and in which the remaining nitrogen substituents correspond to the definitions given for $R_1$, $R_2$, $R_3$ and X in formula I, supra, e.g., cetyldimethylbenzylammonium chloride or cetyldibenzylmethyl ammonium bromide, can also be used as enhancer substances when practicing this invention.

The amount of enhancer substance or mixture of enhancer substances employed when practicing this invention can vary within wide limits depending on the particular enhancer substance(s) chosen, the amount and type of chemiluminescent compound(s) present, etc. For example, certain enhancers, such as BSA, exhibit an optimum concentration, depending primarily on the chemiluminescent compound present, beyond which the addition of further amounts of the enhancer produces no further increase in light intensity. Other enhancers, such as TMQ, provide increased enhancement with increasing concentration. In general, however, amounts of enhancer substance ranging from about 0.01% to about 25%, and preferably from about 0.1% to about 5%, based on the weight of enhancer divided by the weight of aqueous medium, will be employed.

Any chemiluminescent, enzymatically-cleavable; 2-dioxethane compound that (1) can be induced to decompose to yield a moiety in an excited state, such moiety having a heteropolar character that makes it susceptible to environmental effects, and particularly to dampening or diminution of luminescence in a polar protic environment, and that (2) is usable to determine the presence, concentration or structure of a substance in a polar protic environment, particularly a substance in an aqueous sample, can be used in practicing this invention.

1,2-Dioxetanes such as the enzymatically-cleavable dioxetanes disclosed and claimed in the aforementioned copending Bronstein, Bronstein et al and Edwards applications form one class of usable chemiluminescent chemical compounds. These 1,2-dioxetanes can be represented by the general formula:

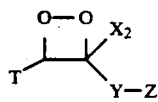
(III)

In this formula T is an unsubsituted or substituted cycloalkyl, aryl, polyaryl or heteroatom group, e.g., an unsubstituted cycloalkyl group having from 6 to 12 ring carbon atoms, inclusive; a substituted cycloalkyl group having from 6 to 12 ring carbon atoms, inclusive, and having one or more substituents which can be an alkyl group having from 1 to 7 carbon atoms, inclusive, or a heteroatom group which can be an alkoxy group having from 1 to 12 carbon atoms, inclusive, such as methoxy or ethoxy, a substituted or unsubstituted aryloxy group, such as phenoxy or carboxyphenoxy, or an alkoxyalkyloxy group, such as methoxyethoxy or polyethyleneoxy, or a cycloalkylidene group bonded to the 3-carbon atom of the dioxetane ring through a spiro linkage and having from 6 to 12 carbon atoms, inclusive, or a fused polycycloalkylidene group bonded to the 3-carbon of the dioxetane ring through a spiro linkage and having two or more fused rings, each having from 5 to 12 carbon atoms, inclusive, e.g., an adamant-2-ylidene group.

The symbol Y represents a light-emitting fluorophore-forming fluorescent chromophore group capable of absorbing energy to form an excited energy state from which it emits optically detectable energy to return to its original energy state.

The symbol $X_2$ represents hydrogen or an alkyl, aryl, aralkyl, alkaryl, heteroalkyl, heteroaryl, cycloalkyl or cycloheteroalkyl group, e.g., a straight or branched chain alkyl group having from 1 to 7 carbon atoms, inclusive; a straight or branched chain hydroxyalkyl group having from 1 to 7 carbon atoms, inclusive, or an —OR group in which R is a $C_1$-$C_{20}$ unbranched or branched, unsubstituted or substituted, saturated or unsaturated alkyl, cycloalkyl, cycloalkenyl, aryl, aralkyl or aralkenyl group, fused ring cycloalkyl, cycloalkenyl, aryl, aralkyl or aralkenyl group, or an N, O or S hetero atom-containing group, or an enzyme-cleavable group containing a bond cleavable by an enzyme to yield an electron-rich moiety bonded to the dioxetane ring. Preferably $X_2$ is a methoxy group.

The symbol Z represents an enzyme-cleavable group containing a bond cleavable by an enzyme to yield an electron-rich moiety bonded to the dioxetane ring, e.g., a bond which, when cleaved, yields an oxygen anion, a sulfur anion or a nitrogen anion, and particularly an amido anion such as a sulfonamido anion.

One or more of the substituents T, $X_2$ and Z can also include a substituent which enhances the water solubility of the 1,2-dioxetane, such as a carboxylic acid, sulfonic acid or quaternary amino salt group, at least one of $X_2$ and Z, and preferably Z, is an enzyme-cleavable group, and preferably an enzyme-cleavable phosphate ester group, and $X_2$ and Y together can represent a fused fluorescent chromophore group bonded to the 4-carbon atom of the dioxetane ring through a spiro linkage, e.g., one having the general formula:

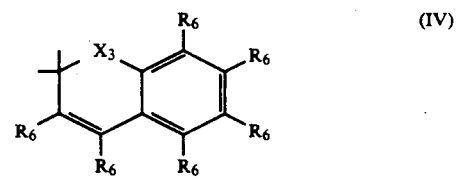
(IV)

In this formula $X_3$ is

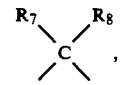

—O—, —S— or —$NR_9$, where each of $R_7$, $R_8$ and $R_9$, independently, is hydrogen, a branched or straight chain alkyl group having 1 to 20 carbon atoms, inclusive, e.g., methyl, n-butyl or decyl, a branched or straight chain heteroalkyl group having 1 to 7 carbon atoms, inclusive, e.g., methoxy, hydroxyethyl or hydroxypropyl; an aryl group having 1 or 2 rings, e.g., phenyl; a heteroaryl group having 1 or 2 rings, e.g., pyrrolyl or pyrazolyl; a cycloalkyl group having 3 to 7 carbon atoms, inclusive, in the ring, e.g., cyclohexyl; a heterocycloalkyl group having 3 to 6 carbon atoms, inclusive, in the ring, e.g., dioxane; an aralkyl group having 1 or 2 rings, e.g., benzyl; an alkaryl group having 1 or 2 rings, e.g., tolyl; or an enzyme-cleavable group as defined above; and each $R_6$, independently, can be hydrogen; an electron-withdrawing group, such as a perfluoroalkyl group having between 1 and 7 carbon atoms, inclusive, e.g., trifluoromethyl; a halogen; $CO_2H$, $Z_1CO_2H$, $SO_3H$, $NO_2$, $Z_1NO_2$, C=N, or $Z_1C=N$, where $Z_1$ is a branched or straight chain alkyl group having 1 to 7 carbon atoms, inclusive, e.g., methyl, or an aryl group having 1 or 2 rings, e.g., phenyl; an electron-donating group, e.g., a branched or straight chain $C_1$-$C_7$ alkoxy group, e.g., methoxy or ethoxy; an aralkoxy group having 1 or 2 rings, e.g., phenoxy; a branched or straight chain $C_1$-$C_7$ hydroxyalkyl group, e.g., hydroxymethyl or hydroxyethyl; a hydroxyaryl group having 1 or 2 rings, e.g., hydroxyphenyl; a branched or straight chain $C_1$-$C_7$ alkyl ester group, e.g., acetate; or an aryl ester group having 1 or 2 rings, e.g., benzoate; a heteroaryl group having 1 or 2 rings, e.g., benzoxazole, benzthiazole, benzimidazole or benztriazole; or hydrogen or an enzyme-cleavable or chemically cleavable group Z as defined herein, with at least one of $R_6$ being Z. Furthermore, all of the $R_6$ groups together can form a ring which can be substituted or unsubstituted, and one or more of the substituents T, $X_2$ and Z can also include a substituent which enhances the water solubility of the 1,2-dioxetane, such as a carboxylic acid, sulfonic acid or quaternary amino salt group.

Included among the substances whose residues can be present in such 1,2-dioxetanes as fluorescent chromophore

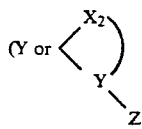

groups are:
anthracene and anthracene derivatives, e.g., 9,10-diphenylanthracene, 9-methylanthracene, 9-anthracene carboxaldehyde, anthrylalcohols and 9-phenylanthracene;
rhodamine and rhodamine derivatives, e.g., rhodols, tetramethyl rhodamine, tetraethyl rhodamine, diphenyldimethyl rhodamine, diphenyldiethyl rhodamine and dinaphthyl rhodamine;
fluorescein and fluorescein derivatives, e.g., 5-iodoacetamido fluoresoein, 6-iodoacetamido fluorescein and fluorescein-5-maleimide;
coumarin and coumarin derivatives, e.g., 7-dialkylamino-4-methylcoumarin, 4-bromomethyl-7-methoxycoumarin and 4-bromomethyl-7-hydroxy coumarin;
erythrosin and erythrosin derivatives, e.g., hydroxy erythrosins, erythrosin-5-iodoacetamide and erythrosin-5maleimide;
aciridine and aciridine derivatives, e.g., hydroxy aciridines and 9 methyl aciridine;
pyrene and pyrene derivatives, e.g., N-(1-pyrene) iodoacetamide, hydroxy pyrenes and 1-pyrenemethyl iodoacetate;
stilbene and stilbene derivatives, e.g., 6,6'-dibromostilbene and hydroxy stilbenes;
naphthalene and naphthalene derivatives, e.g., 5-dimethylamino naphthalene-1-sulfonic acid and hydroxy naphthalenes;
nitrobenzoxadiazoles and nitrobenzoxadiazole derivatives, e.g., hydroxy nitrobenzoxadiazoles, 4-chloro-7-nitrobenz-2-oxa-1,3-diazole, 2-(7-nitrobenz-2-oxa-1,3-diazol-4-yl) methylaminoacetaldehyde and 6-(7-nitrobenz-2-oxa-1,3-diazol-4-ylaminohexanoic acid;
quinoline and quinoline derivatives, e.g., 6-hydroxyquinoline and 6-aminoquinoline;
acridine and acridine derivatives, e.g., N-methylacridine and N-phenylacridine;
acidoacridine and acidoacridine derivatives, e.g., 9-methylacidoacridine and hydroxy-9-methylacidoacridine;
carbazole and carbazole derivatives, e.g., N-methylcarbazole and hydroxy-N-methylcarbazole;
fluorescent cyanines, e.g., DCM (a laser dye), hydroxy cyanines, 1,6-diphenyl-1,3,5-hexatriene, 1-(4-dimethyl aminophenyl)-6-phenylhexatriene and the corresponding 1,3butadienes;
carbocyanines and carbocyanine derivatives, e.g., phenylcarbocyanine and hydroxy carbocyanines;
pyridinium salts, e.g., 4(4-dialkyldiaminostyryl)N-methyl pyridinium iodate and hydroxy-substituted pyridinium salts;
oxonols; and
resorofins and hydroxy resorofins.

Cleavage of an enzymatically-cleavable 1,2-dioxetane can be accomplished using an enzyme such as an alkaline phosphatase that will cleave a bond in, for example, a Z substituent such as a phosphate ester group to produce a Y anion in a charge transfer state that will, in turn, destabilize the dioxetane and cleave its oxygen-oxygen bond. Cleavage can also be accomplished by using an enzyme such as an oxidoreductase enzyme that will cleave the oxygen-oxygen bond directly; see the aforementioned Bronstein and Bronstein et al pending U.S. patent applications.

Besides a phosphate ester group, Z in formulas III and IV above can be an enzyme-cleavable alkanoyloxy group, e.g., an acetate ester group, or an oxacarboxylate group, 1-phospho-2,3-diacylglyceride group, 1-thio-D-glucoside group, adenosine triphosphate analog group, adenosine diphosphate analog group, adenosine monophosphate analog group, adenosine analog group, $\alpha$-D-galactoside group, $\beta$-D-galactoside group, $\alpha$-D-glucoside group, $\beta$-D-glucoside group, $\alpha$-D-mannoside group, $\beta$-D-mannoside group, 62 -D-fructofuranoside group, $\beta$-D-glucosiduronate group, p-toluenesulfonyl-L-arginine dye ester group or p-toluenesulfonyl-L-arginine dye amide group.

Preferred enzymatically-cleavable 1,2-dioxetanes for use in practicing this invention are the 3-(2'-spiroadamantane)-4-methoxy-4-(3''-phosphoroyloxy)-phenyl-1,2-dioxetane salts represented by the formula:

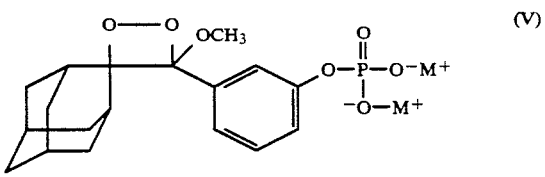

wherein M+ represents a cation such as alkali metal, e.g., sodium or potassium, ammonium, or a $C_1$–$C_7$ alkyl, aralkyl or aromatic quaternary ammonium cation, $N(R_5)_4^+$ in which each $R_5$ can be alkyl, e.g., methyl or ethyl, aralkyl, e.g., benzyl, or form part of a heterocyclic ring system, e.g., pyridinium, and particularly the disodium salt.

One or more auxiliary fluorophores extraneous to the light-emitting fluorophores produced by the decomposition of the chemiluminescent compound(s) also present that will accept energy, especially light, from energy-emitting fluorophores produced by the decomposition of the chemiluminescent compound(s) and in turn emit detectable energy, again preferably light, can be used when practicing this invention. Among the auxiliary fluorophores that can be used, alone or in combination, are the substances listed above whose residues can be present in 1,2-dioxetanes as fluorescent chromophore groups. Fluorescein and fluorescein derivatives, including derivatives capable of establishing a covalent bond with the enhancer substance, are especially preferred for use as the auxiliary fluorophore(s).

These auxiliary fluorophores can simply be admixed with the enhancer substance(s) and chemiluminescent compound(s) or bonded to either or both of these materials. When the auxiliary fluorophore is bonded to a chemiluminescent compound, it is preferably bonded to the portion of the chemiluminescent compound that, upon decomposition, forms a fragment containing the fluorophore portion of the chemiluminescent compound's molecule. In this way energy transfer is enhanced due to the two fluorophores being in close proximity to one another. Auxiliary fluorophores that are insoluble or partially insoluble in aqueous medium can be solubilized by first grafting them onto solubilizing molecules, e.g., water soluble oligomer or polymer molecules.

When admixed with the enhancer substance(s) and chemiluminescent compounds(s), the amount of auxiliary fluorophore present used can range from about 1 ng (nanogram)/mL to about 10 mg/mL of enhancer-containing solution, and preferably from about 1 μg/mL to about 100 μg/mL of enhancer-containing solution.

When auxiliary fluorophores covalently attached to proteins are used, the molar ratio of fluorophore to protein can range from 1 to 60, and preferably (e.g., for BSA) from 1 to 6, per molecule of protein.

This invention is particularly useful when conducting immunoassays, such as those employed to detect an enzyme or a member of a specific binding pair, e.g., an antigen-antibody pair or a nucleic acid paired with a probe capable of binding to all or a portion of the nucleic acid. Such assays include immunoassays used to detect a hormone such as β-human chorionic gonadotropin (β-hCG), thyroid stimulating hormone (TSH), follicle stimulating hormone (FSH), luteinizing hormone (LH) or the like, cell surface receptor assays, and nucleic acid assays used to detect viruses, e.g., HIV or HTLV III and cytomegalovirus, or bacteria, e.g., E.-Coli., and histocompatibility assays; for typical assay protocols see the working examples, infra, as well as the aforementioned Bronstein and Bronstein et al U.S. patent applications. The invention can also be used in assays for a chemical analyte, such as potassium or sodium ions, or in assays for substances such as cholesterol or glucose in which the analyte is caused to decompose, for example using an enzyme such as cholesterol oxidase or glucose oxidase, to form a substance, e.g., hydrogen peroxide, capable of causing the chemiluminescent compound to decompose.

In order that those skilled in the art can more fully understand this invention, the following examples are set forth. These examples are given solely for purposes of illustration, and should not be considered as expressing limitations unless so set forth in the appended claims.

EXAMPLES 1–45

The enhancer substances listed in Table I below, in which all parts and percentages are by weight, unless otherwise stated, were evaluated for their light intensity-enhancing properties by dissolving the appropriate amount of enhancer in 0.05M carbonate buffer solution containing 1 mM magnesium chloride (pH=9.5) to give the noted concentrations. To 1 ml samples of each of the resulting solutions (including the control, Example 31, containing no enhancer) there was then added sufficient 3-(2'-spiroadamantane)-4-methoxy-4-(3''-phosphoryloxy)phenyl-1,2-dioxetane disodium salt, dissolved in the same carbonate buffer solution used to dissolve the enhancer, to give a final concentration of this chemiluminescent compound of 0.125 mM. The resulting solutions were then equilibrated to 30° C., after which aqueous alkaline phosphatase solution was added to give a final enzyme concentration of $4.17 \times 10^{-10}$M. The luminescence signal of each solution was then measured at 30° C. in a Turner 20 E Luminometer integrating over twenty minutes. Successful enhancers or amounts of enhancer were those that gave an enhancement factor greater than 1 (i.e., greater than that of the sample, Example 30, containing the chemiluminescent compound but no enhancer).

TABLE I

| Example | Enhancer Concentration | Enhancement Factor |
|---|---|---|
| 1 | 0.1% BDMQ + fluoroscein[1] | 298.891832 |
| 2 | 0.1% BDMCAC[2] + fluorescein[1] | 135.643835 |
| 3 | 1.0% BDMQ | 19.026097 |
| 4 | 0.1% BDMQ | 18.422605 |
| 5 | 0.25% TMQ | 7.194016 |
| 6 | 0.1% BSA | 5.172073 |
| 7 | 1.0% BSA | 4.790837 |
| 8 | 0.1% TMQ | 4.475993 |
| 9 | 0.1% BDMCAC | 2.874500 |
| 10 | 1.0% PolyMAPTAC[3] | 2.384163 |
| 11 | 1.0 PVP K-90[4] | 2.034744 |
| 12 | 0.01 μg/ml fluorescein alone | 2.004920 |
| 13 | 1.0% PEOX[5] | 1.454102 |
| 14 | 1.0% PVP K-30[6] | 1.419595 |
| 15 | 1.0% Polybrene[7] | 1.391839 |
| 16 | 0.1% Protein A[8] + fluorescein | 1.391196 |
| 17 | 1.0% PEI 1000[9] | 1.262907 |
| 18 | 1.0% Polyox N-80[10] | 1.167327 |
| 19 | 0.1% PolyMAPTAC | 1.140866 |
| 20 | 0.1% Polybrene | 1.139414 |
| 21 | 0.1% PVP K-30 | 1.112314 |
| 22 | 0.1% PVP K-90 | 1.091996 |
| 23 | 0.1% Kelcosol Algin[11] | 1.084700 |
| 24 | 0.1% Kelco SCS XL[12] | 1.077093 |
| 25 | 0.1% Pluronic F127[13] | 1.076141 |
| 26 | 1.0% Polyox N-10[14] | 1.045022 |
| 27 | 1.0% Kelco SCS XL | 1.043893 |
| 28 | 0.1% PEOX | 1.025682 |
| 29 | 0.1% PEI 1000 | 1.023954 |
| 30 | Buffer solution alone (no enhancer) | 1.00000 |
| 31 | 1.0% Pluronic F127 | 0.959475 |
| 32 | 0.1% 18-crown-6 ether[15] | 0.953054 |
| 33 | 0.1% Gum Ghatti[16] | 0.946162 |
| 34 | 0.1% Protein A | 0.940106 |
| 35 | 0.1% PVHP[17] | 0.933433 |
| 36 | 0.1% Polyox N-80 | 0.930873 |
| 37 | 0.1% Polyox N-10 | 0.907289 |
| 38 | 1.0% PEG[18] | 0.893920 |
| 39 | 1.0% 18-crown-6 ether | 0.871326 |
| 40 | 1.0% Kelcosol Algin[19] | 0.786052 |
| 41 | 0.1% Polyox N-301[20] | 0.765806 |
| 42 | 0.1% PEG | 0.751353 |
| 43 | 1.0% Gum Ghatti | 0.558062 |
| 44 | 1.0% Polyox N-301 | 0.523886 |
| 45 | 1.0% PVHP | 0.029226 |

Figure 2:
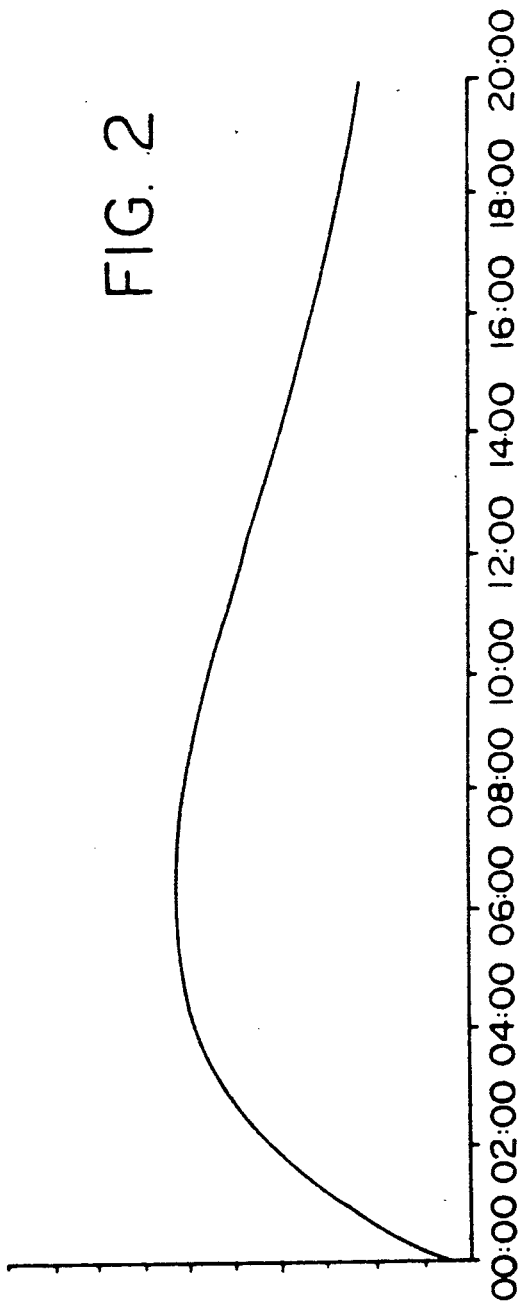
FIGS. 2-4 show the luminescence rate spectra of the emitting dioxetane fragment with and without enhancer: evaluated in Example 4 (0.1% BDMQ.
Figure 3:
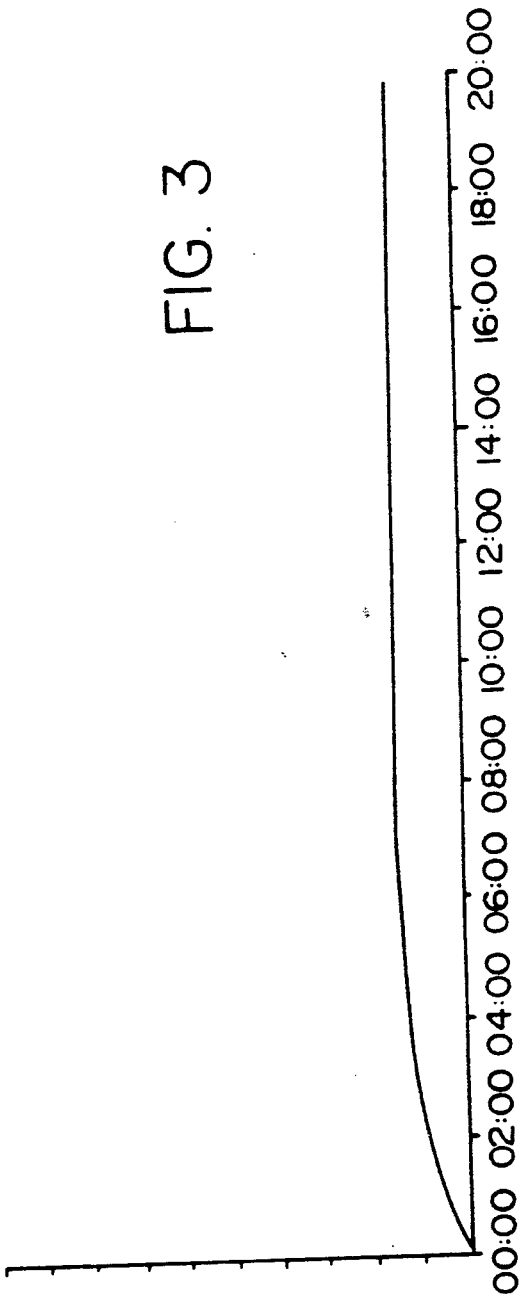
Figure 4:
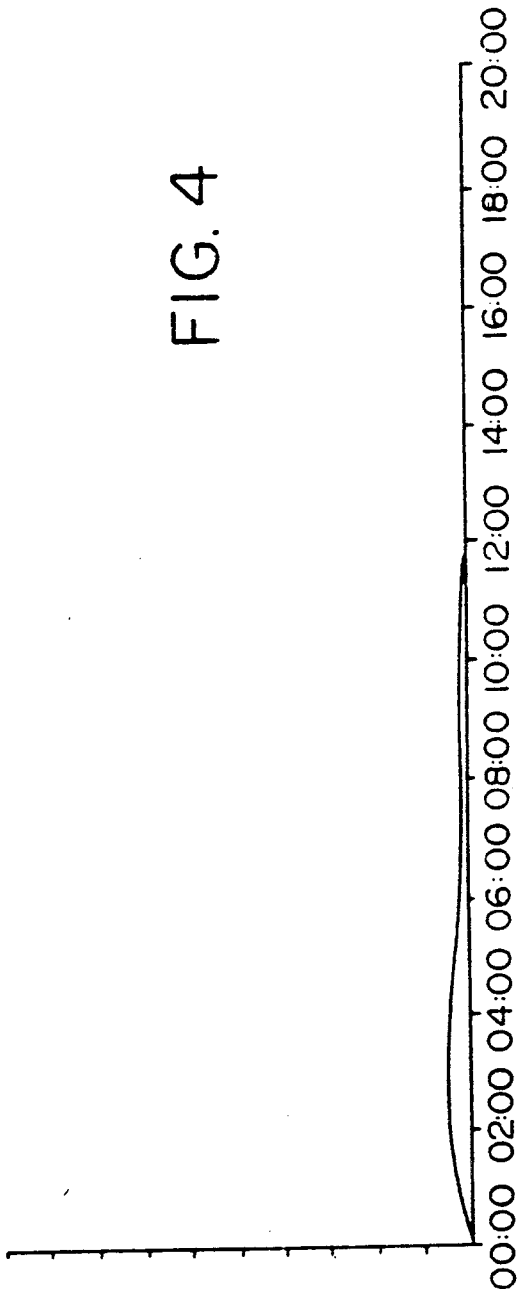
Figure 5:
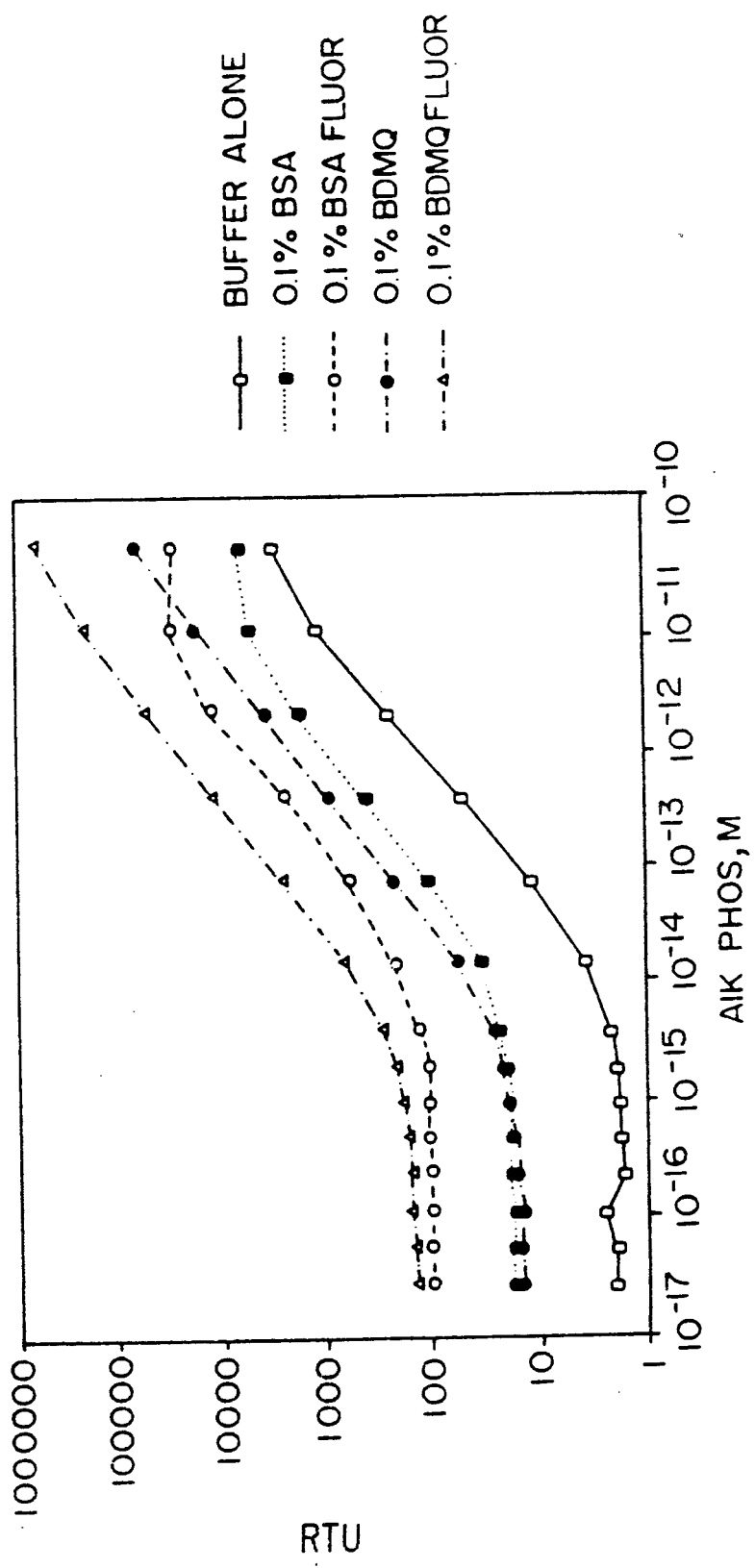
FIG. 5 shows a plot of Relative Turner Units (RTU) versus alkaline phosphatase concentration for the various systems of Example 47.

[1]0.01 μg/ml Fluorescein added.
[2]Benzyldimethylcetylammonium chloride; TCI.
[3]Polymethacrylamidopropylenemethyl ammonium chloride; Polyscience.
[4]Polyvinylpyrrolidone; GAF.
[5]Polyethyloxazoline; Dow Chemical Co.
[6]Polyvinylpyrrolidoinone; CTAF.
[7]1,5-Dimethyl-1,5-diaza-undecamethylene polymethobromide; Aldrich.
[8]Staphylococcus-derived; Sigma.
[9]Polyethyleneimine; Dow Chemical Co.
[10]Polyethyleneoxide, Union Carbide Corp.
[11]Alginic acid (sodium salt); Merck.
[12]Sodium cellulose sulfate; Merck.
[13]Polyethylenepropylene glycol; BASF Wyandotte.
[14]Polyoxazoline; Dow Chemical Co.
[15]1,4,7,10,13,16-hexaoxacyclooctadecane; Aldrich.
[16]Cat. No. GO378; Sigma.
[17]Polyvinylhydrogenphthalate; Eastman Kodak 5527.
[18]Polyethylene glycol, molecular weight 8000, for biological use, P2139; Sigma.
[19]Alginate; Kelco Co.
[20]Polyethylene oxide; Union Carbide The light emission spectra of the samples of Examples 4, 7 and 30 are shown in FIGS. 2, 3 and 4, respectively, with light intensity being measured on the abscissa (X axis) and time on the ordinate (Y axis) of each plot.

EXAMPLE 46

A TSH assay was carried out as follows:

Materials

Mouse monoclonal anti-TSH-$\beta$ antibody was used to coat $\frac{1}{8}$ inch beads for analyte capture. Mouse monoclonal anti-TSH antibody was conjugated with alkaline phosphatase and used as a detection antibody.

TSH was obtained from Calbiochem, Catalog No. 609396, and BSA (type V—fatty acid free) was obtained from Sigma, Catalog No. A6003.

The buffer solution used for the analyte and conjugate contained 0.1M Tris-HCI, 1mM $MgCl_2$, and 2% by weight BSA (pH=7.5) The substrate buffer solution contained 0.1M Tris, 0.1 mM $MgCl_2$, 0.1% by weight BSA (pH=9.5), and 3-(2'-spiroadamantane)-4-methoxy-4-(3''-phos phoryloxy)phenyl-1,2-dioxetane disodium salt as the chemiluminescent compound. (50 $\mu g/ml$).

Protocol

15$\mu$l of a TSH-containing analyte solution was mixed with 135$\mu$l of conjugate antibody solution. Two $\frac{1}{8}$ inch beads coated as described above were added to the solution and incubated for 2 hours at 23° C. The beads were then washed four times with 0.1M Tris (pH=7.5) and transferred to a reaction tube. 200$\mu$l of the same chemiluminescent compound used in the substrate buffer solution described above was added to the tube. Following an incubation period of 20 minutes, light emission was recorded as ten second counts using a Berthold Clinilumat Luminescence Analyzer.

An identical TSH assay was also performed with the same concentration of substrate in the same buffer without BSA for the sake of comparison. As shown in FIG. 1, a plot of the data in Table II below, the BSA-containing sample (Curve A) showed greater luminescence intensity for a given TSH concentration than the sample without BSA (Curve B).

TABLE II

| TSH Concentration ($\mu U/ml$) | Luminescent Signal With 0.10% BSA | (Counts/$10$ sec $\times 10^{-4}$) Without BSA |
| --- | --- | --- |
| 1 | 0.48 | 0.25 |
| 2 | 1.1 | 0.49 |
| 4 | 1.7 | 1.1 |

EXAMPLE 47

An assay for alkaline phosphatase was conducted in the following manner.

Components

Buffer: 0.05M carbonate, 1mM $MgCl_2$ at pH 9.5
Substrate: 3-(2'-spiroadamantane)-4-methoxy-4-(3''-phosphoryloxy)phenyl-1,2-dioxetane disodium salt at 0.4 mM concentration
Alkaline Phosphatase: stock solution at 1.168 $\mu g/ml$ in the buffer
Enhancing Systems Tested:
 1. Buffer alone, control
 2. Buffer plus 0.1% BSA
 3. Buffer plus 0.1% BSA-fluorescein (BSA to fluorescein molar ratio of 1 to 3)
 4. Buffer plus 0.1% BDMQ
 5. Buffer plus 0.1% BDMQ and fluorescein (0.01 mg of fluorescein disodium salt added per ml of BDMQ).

Serial dilutions of alkaline phosphatase stock solutions were made in tubes with final enzyme concentrations of:

| | |
| --- | --- |
| $4.17 \times 10^{-11}M$ | $1.67 \times 10^{-15}M$ |
| $8.34 \times 10^{-12}M$ | $8.34 \times 10^{-16}M$ |
| $1.67 \times 10^{-12}M$ | $4.17 \times 10^{-16}M$ |
| $3.34 \times 10^{-13}M$ | $2.09 \times 10^{-16}M$ |
| $6.68 \times 10^{-14}M$ | $1.0 \times 10^{-16}M$ |
| $1.34 \times 10^{-14}M$ | $5.0 \times 10^{-17}M$ |
| $3.34 \times 10^{-15}M$ | $2.5 \times 10^{-17}M$ |

Procedure

Duplicate tubes at each of the above concentrations of alkaline phosphatase also containing 0.4 mM 3-(2'-spiroadamantane)-4-methoxy-4-(3''-phosphoryloxy)-phenyl-1,2-dioxetane disodium salt in various enhancing systems were incubated at 30° C. Systems 1, 4 and 5 were incubated for 20 minutes, while systems 2 and 3 were incubated for 80 minutes.

After incubation, 30 second light integrals were measured in a Turner 20E Luminometer, and the effect of the enhancers tested on the limits of detection of alkaline phosphatase is shown in Table IV.

TABLE IV

| Addition | Concentration of Alkaline Phosphatase for 2X Background | Minimum Detectable Conc. of Alkaline Phosphatase |
| --- | --- | --- |
| None | $1.0 \times 10^{-14}M$ | $1.67 \times 10^{-15}M$ (1.12) |
| 0.1% BSA | $9.5 \times 10^{-15}M$ | $8.34 \times 10^{-16}M$ (1.06) |
| 0.1% BSA:Fluorescein | $1.3 \times 10^{-15}M$ | $4.17 \times 10^{-16}M$ (1.04) |
| 0.1% BDMQ | $4.0 \times 10^{-15}M$ | $1.00 \times 10^{-16}M$ (1.07) |
| 0.1% BDMQ:Fluorescein | $3.4 \times 10^{-15}M$ | $2.09 \times 10^{-16}M$ (1.06) |

1 Buffer: 0.05M Carbonate, 1 mM $MgCl_2$, pH = 9.5.
Temperature: 30° C. Chemiluminescent compound concentration is 0.4 mM.
2 The number in parentheses is the multiple of background at the indicated concentration.

EXAMPLE 48

The ability to detect luminescense photographically by means of this invention was demonstrated in the following manner.

Components

Buffer: 0.1M Tris, 1 mM $MgCl_2$ at pH 9.8 prepared with 0.1% BSA and without BSA, (BSA purchased from Sigma, Catalog number A7906).
Enzyme: 0.05 $\mu g$ Alkaline Phosphatase ($3.6 \times 10^{-13}$ moles) purchased from Biozyme Corporation.
Membrane: 0.45 $\mu$ pore-size nitrocellulose.
Substrate: 3-(2'-spiroadamantane)-4-methoxy-4-(3''-phosphoryloxy)phenyl-1,2-dioxetane disodium salt at 0.08 mM concentration.

Protocol

Enzyme solution was spotted on a dry nitrocellulose membrane. Subsequently, the membrane was blocked with 2.5% dry milk solids and 1% fish gelatin in phosphate buffered saline at pH 7.3. The blocked membrane was washed with the substrate solution in buffers containing no BSA, and with BSA.

Figure 6:
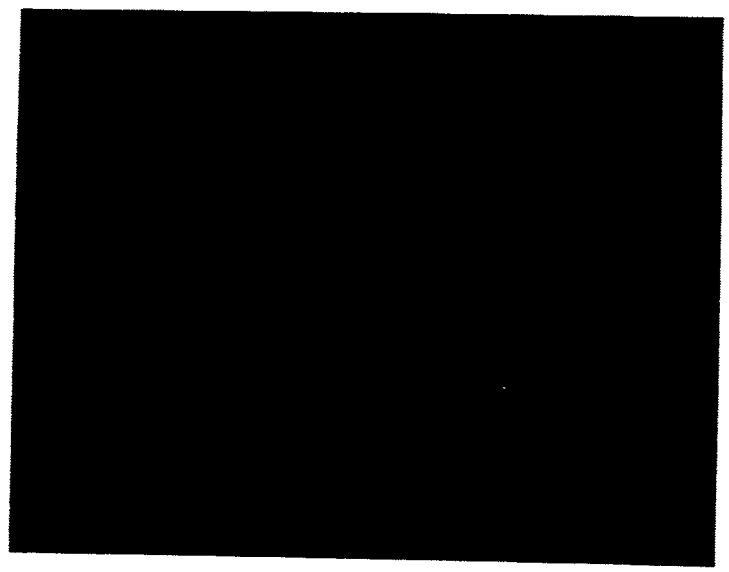
FIGS. 6 and 7 are reproductions of the photographs described in Example 48 taken of a substrate solution without (FIG. 6) and with (FIG. 7) BSA enhancer.
Figure 7:
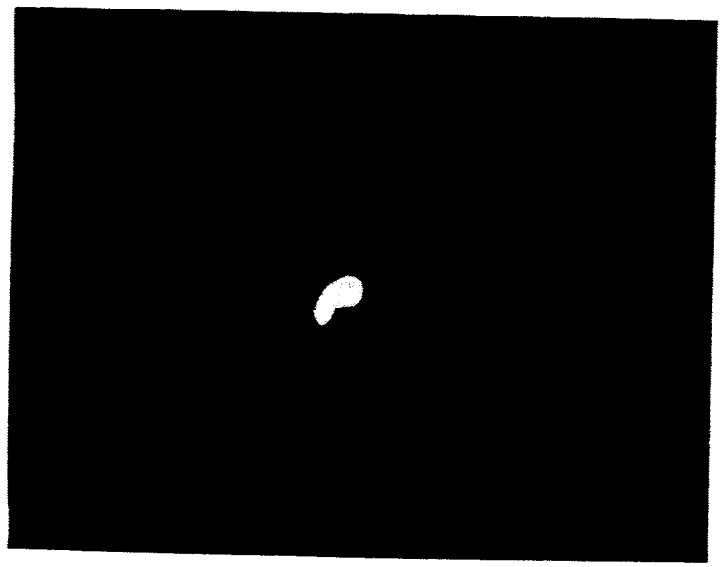

The membrane was placed in a camera luminometer and 10 minute exposures were recorded on Type 612 Polaroid Black and White Instant Film Reproductions of the photographs obtained appear as FIGS. 6 and 7.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. In a process carried out in an aqueous medium in which electromagnetic energy released by the enzyme-activated decomposition of an enzymatically cleavable chemiluminescent 1,2-dioxetane to produce an anionic electromagnetic energy-emitting fluorophore is detected to determine the presence, concentration or structure of an analyte, the improvement comprising carrying out the process in the presence of an amount of an admixed water soluble macromolecular enhancer substance sufficient to enhance the intensity of any released detectable electromagnetic energy over the intensity of any detectable electromagnetic energy released in the absence of the enhancer substance, wherein the enhancer substance is itself incapable of energy transfer.

2. The process of claim 1 in which the macromolecular enhancer substance has the ability to inhibit the fluorophore from releasing energy through non-light emitting pathways.

3. The process of claim 2 in which the macromolecular enhancer substrate comprises a naturally-occurring or synthetic macromolecular substance that can provide a hydrophobic microenvironment for the fluorophore.

4. The process of claim 3 in which the macromolecular enhancer substance comprises a naturally-occurring macromolecular substance.

5. The process of claim 4 in which the macromolecular substance is a globular protein that includes hydrophobic regions.

6. The process of claim 5 in which the globular protein is a mammalian serum albumin.

7. The process of claim 6 in which the serum albumin is bovine serum albumin.

8. The process of claim 6 in which the serum albumin is human serum albumin.

9. The process of claim 5 in which the globular protein is mammalian IgG.

10. The process of claim 5 in which the globular protein is Protein A.

11. The process of claim 3 in which the macromolecular enhancer substance comprises a synthetic macromolecular substance.

12. The process of claim 11 in which the macromolecular enhancer substance comprises an oligomeric or polymeric quaternary ammonium salt.

13. The process of claim 12 in which the quaternary ammonium salt is a poly(vinylaryl quaternary ammonium salt).

14. The process of claim 13 in which the poly(vinylaryl quaternary ammonium salt) is poly(vinylbenzyltrimethylammonium chloride).

15. The process of claim 13 in which the poly(vinylaryl quaternary ammonium salt) is poly(vinylbenzyl(benzyldimethylammonium chloride)).

16. The process of claim 1 in which the 1,2-dioxetane is a 3-(2'spiroadamantane)-4-methoxy-(3"-phosphoryloxy)phenyl-1,2-dioxetane salt.

17. The process of claim 1 further comprising carrying out the process in the presence of an admixed auxiliary fluorophöre extraneous to the electromagnetic energy-emitting fluorophore produced by the decomposition of the chemiluminescent 1,2-dioxetane, the auxiliary fluorophore being capable of accepting energy from the electromagnetic energy-emitting fluorophore to in turn emit detectable energy.

18. The process of claim 17 in which the auxiliary fluorophore is admixed with the chemiluminescent 1,2-dioxetane and the macromolecular enhancer substance.

19. The process of claim 18 in which the auxiliary fluorophore is a fluorescein.

20. The process of claim 17 in which the auxiliary fluorophore is covalently bonded to the portion of the chemiluminescent 1.2-dioxetane that, upon decomposition, produces the electromagnetic energy-emitting fluorophore.

21. The process of claim 20 in which the auxiliary fluorophore is a fluorescein.

22. The process of claim 17 in which the auxiliary fluorophore is covalently bonded to the macromolecular enhancer substance.

23. The process of claim 22 in which the auxiliary fluorophore is a derivatized fluorescein capable of establishing a covalent bond with the macromolecular enhancer substance.

24. The process of any one of claims 1, 17 or 22 in which the process carried out is a step in an immunoassay.

25. The process of claim 24 in which the immunoassay is for the detection of a specific binding pair comprising an antigen and an antibody, there being bonded to either or both of the antigen and the antibody a label.

26. The process of claim 25 in which the label used in the immunoassay is an enzyme.

27. The process of claim 24 in which the immunoassay is for the detection of an enzyme.

28. The process of claim 24 in which the immunoassay is for the detection of a hormone.

29. The process of any one of claims 1, 17 or 22 in which the process carried out is a step in a chemical assay.

30. The process of claim 29 in which the chemical substance is cholesterol.

31. The process of claim 29 in which the chemical substance is glucose.

32. The process of any one of claims 1, 17 or 22 in which the process carried out is a nucleic acid probe assay.

33. The process of claim 32 in which the nucleic acid probe assay is for the detection of a virus.

34. The process of claim 32 in which the nucleic acid probe assay is for the detection of a bacteria.

35. The process of any one of claims 1, 17 or 22 in which the process carried out is a histocompatibility assay.

36. The process of any one of claims 1, 17 or 22 in which the process carried out is a technique for studying the microstructure of a macromolecule.

* * * * *

UNITED STATES PATENT AND TRADEMARK OFFICE
CERTIFICATE OF CORRECTION

PATENT NO. : 5,145,772

DATED : September 8, 1992

INVENTOR(S) : John C. Voyta et al.

It is certified that error appears in the above-identified patent and that said Letters Patent is hereby corrected as shown below:

On the Title Page, Item [75] Inventors: Patricia McGroth, Cambridge, should be deleted as the fourth inventor.

On the Title page,

Item [63] Related U.S. Application Data, should read, --Continuation of Ser. No. 203,263, June 1, 1988, now abandoned, which is a Continuation-in-part of Ser. No. 889,823, June 24, 1986, pending--.

Signed and Sealed this

Nineteenth Day of October, 1993

Attest:

BRUCE LEHMAN

Attesting Officer

Commissioner of Patents and Trademarks